United States Patent [19]

Jenner et al.

[11] Patent Number: 4,602,851
[45] Date of Patent: Jul. 29, 1986

[54] DISUBSTITUTED ETHANES AND THEIR USE IN LIQUID CRYSTAL MATERIALS AND DEVICES

[75] Inventors: John A. Jenner, Wimborne; Ian C. Sage, Poole; Robert A. Smith, Malvern, all of England

[73] Assignee: The Secretary of State for Defence in Her Britannic Majesty's Government of the United Kingdom of Great Britain and Northern Ireland, London, England

[21] Appl. No.: 609,134

[22] Filed: May 11, 1984

[30] Foreign Application Priority Data

May 20, 1983 [GB] United Kingdom ............. 8314077

[51] Int. Cl.⁴ .................. G02F 1/13; C09K 3/34; C07C 69/84
[52] U.S. Cl. .................. 350/350 R; 252/299.63; 558/416; 560/8
[58] Field of Search .............. 260/465 D; 560/8; 562/405; 252/299.62, 299.63; 350/350 R

[56] References Cited

U.S. PATENT DOCUMENTS 4,439,015  3/1984  Rich et al. ................. 350/350 R

OTHER PUBLICATIONS

DIC Liquid Crystal Materials and the Mixtures by Dainippon Ink & Chemicals Jan. 28, 1983.

Primary Examiner—Dolph H. Torrence
Attorney, Agent, or Firm—Stevens, Davis, Miller & Mosher

[57] ABSTRACT

Disubstituted ethanes having a formula

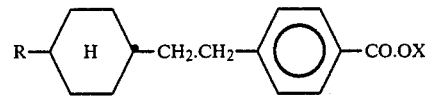

wherein R is alkyl, X is selected from hydrogen,

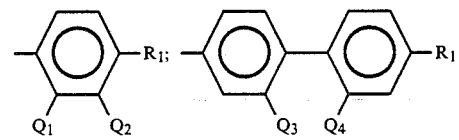

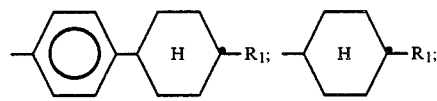

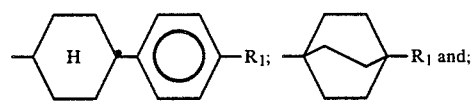

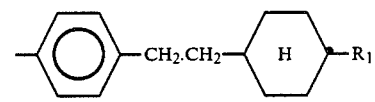

wherein each $R_1$ is selected from H, alkyl, alkoxy, halo and cyano and each of $Q_1$, $Q_2$, $Q_3$ and $Q_4$ is independently selected from H and F are useful as components of liquid crystal materials for electro-optical displays and compounds useful in the production of such components.

10 Claims, 7 Drawing Figures

DISUBSTITUTED ETHANES AND THEIR USE IN LIQUID CRYSTAL MATERIALS AND DEVICES

The present invention relates to disubstituted ethanes and their use in liquid crystal materials and devices and in the production of liquid crystal materials.

The use of liquid crystal materials to exhibit electro-optical effects in display devices such as digital calculators, watches, meters and simple word displays is now well known. However known liquid crystal materials are not ideal in all respects and a considerable amount of work is currently being carried out in the art to improve their properties.

Liquid crystal materials normally consist of specially selected mixture compositions and improved materials are obtained by forming new mixtures having an improved combination of properties.

According to the present invention in a first aspect there is provided a novel carboxylic acid suitable for use in the production of liquid crystal compounds which has the formula:

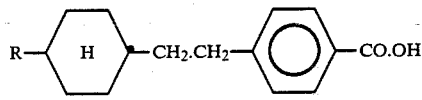

Formula I

According to the present invention in a second aspect there is provided a method of use of a compound of Formula I specified above which comprises producing a liquid crystal compound which is an ester of the acid of Formula I by esterifying the acid or a derivative thereof with an appropriate alcohol.

According to the present invention in a third aspect there is provided a liquid crystal ester produced by the method of the second aspect which has the formula:

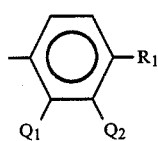

Formula II where X is an optionally substituted aryl or alicyclic ring structure and R is alkyl.

Preferably, X in Formula II is selected from optionally substituted phenyl, biphenyl, cyclohexyl, bicyclohexyl, cyclohexylphenyl and bicyclo-octyl radicals.

Particularly preferred structures for X are as follows:

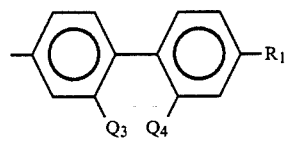

(i)

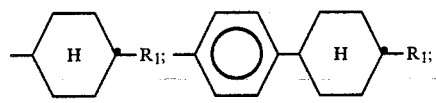

(ii)

where $R_1$ is as defined above and $Q_3$ and $Q_4$ is each independently selected from H and fluorine.

Other possible groupings for the radical X in Formula II are as follows:

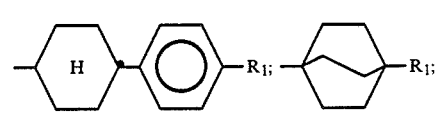

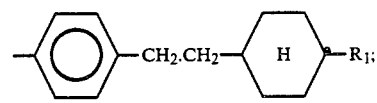

where $R_1$ is as defined above,

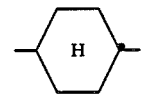

represents a trans-1,4-disubstituted cyclohexane ring,

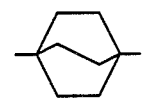

represents a 1,4-disubstituted bicyclo (2,2,2) octane ring.

Particularly preferred groups for the radical $R_1$ are alkyl and cyano.

Where R or $R_1$ is or includes an alkyl group the alkyl group is preferably n-alkyl having from 1 to 12 carbon atoms although it could also be a branched chain group, eg containing a chiral centre.

Where $R_1$ is a halogen it is preferably fluorine or chlorine.

The carboxylic acids of Formula I may be prepared from the corresponding cyano compounds (which are the subject of UK Pat. No. 2023136B) by hydrolysis, eg in acid solution. The cyano compounds have the following formula:

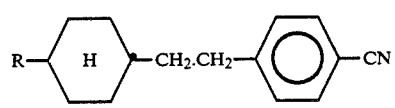

Formula A

The acids of Formula I may be reacted together with the appropriate alcohols of the formula X—OH (where X is defined above) to form the required esters of Formula II by any known esterification method, for example under the catalytic influence of trifluoroacetic anhydride or boric acid and sulpheric acid. Alternatively the acids of Formula I may be converted into acid derivatives, eg acid chlorides which may be reacted with the alcohols X—OH in the presence of a base.

Examples of the preparation of esters of Formula II by such routes which involve known procedures per se are given below.

The esters of Formula II are valuable components of liquid crystal materials (mixtures) for use in electro-optical displays. Typically they have a high clearing point, $T_{N-I}$, (liquid crystal-to-liquid transition temperature) eg >100° C. and are useful in raising the clearing point of mixtures to which they are added.

Thus, the acids of Formula I provide valuable precursors to a variety of liquid crystalline esters particularly those of Formula II.

The compounds of Formula II may be used in applications other than electro-optical applications which are known to be suitable for the use of nematic or chiral nematic liquid crystal compounds. For example, the compounds of Formula II may be incorporated as high clearing point components of temperature sensitive, eg thermochromic, materials, eg for use in the applications described in UK Published Patent Application Nos. 2083244A and 2085585A.

The compounds of Formula II, wherein $R_1$ is H, alkyl or alkoxy and $Q_1$ and $Q_2$ where present are H, generally have a relatively small dielectric anisotropy and may be added to liquid crystal materials of (greater) positive or negative dielectric anisotropy, known and referred to herein respectively as "positive" or "negative" materials in order to produce a mixture having amongst other things a suitable dielectric anisotropy. As is well known to those skilled in the art the dielectric anisotropy of the liquid crystal material is necessary to give electro-optical operation and its sign (for a given frequency) is chosen according to the kind of electro-optical device in which the material is to be used.

The compounds of Formula II wherein $R_1$ is F, Cl or CN generally have a positive dielectric anisotropy (and are strongly positive where $R_1$ is CN).

The compounds of Formula II (i) having $Q_1$ and/or $Q_2$=F, Cl or CN are generally negative materials (and are strongly negative where $Q_1$ and/or $Q_2$ is CN). Likewise the compounds of Formula II (ii) having $Q_3$ and/or $Q_4$=F are generaly (weakly) negative materials.

Where compounds of Formula II are added to strongly positive materials, eg to extend the clearing point of the materials compounds of reasonably low melting point are preferred as the strongly positive (high dielectric anisotropy) components. For example, the compounds of the following known classes are suitable as positive materials:

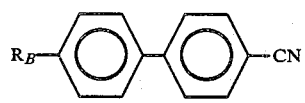

Formula IIIa

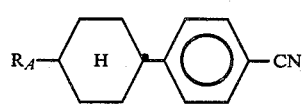

Formula IIIb

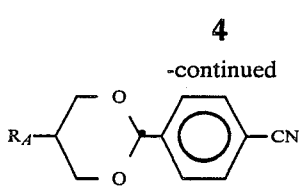

Formula IIIc

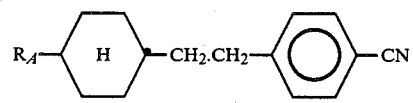

Formula IIId

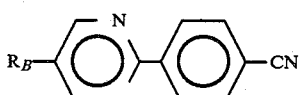

Formula IIIe

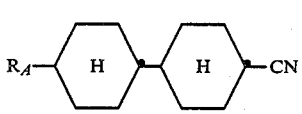

Formula IIIf

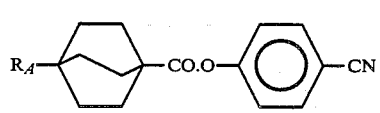

Formula IIIg

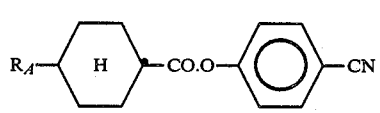

Formula IIIh

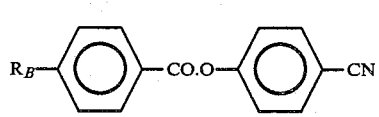

Formula IIIi where each $R_B$ is independently n-alkyl or n-alkoxy and each $R_A$ is independently n-alkyl.

Alternatively, or additionally, the compounds of Formula II may be added to known small dielectric anisotropy compounds, eg to raise the clearing point of the overall mixture. The following classes are examples of known compounds of generally small dielectric anisotropy of reasonably low melting point:

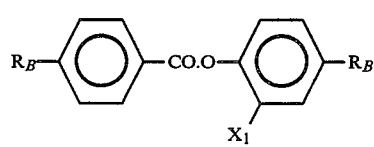

Formula IVa

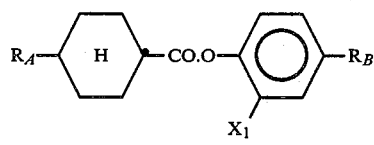

Formula IVb

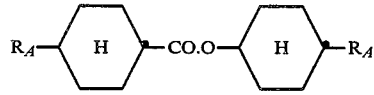

Formula IVc

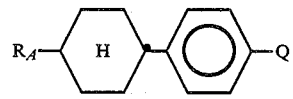

Formula IVd

-continued

Formula IVe
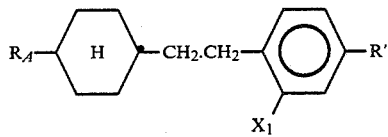

Formula IVf
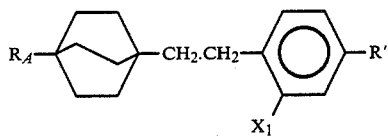

Formula IVg
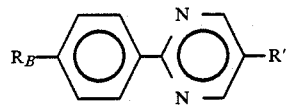

Formula IVh
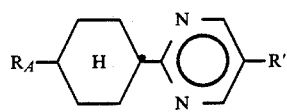

Formula IVi
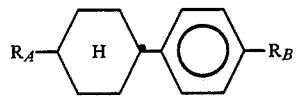

Formula IVj
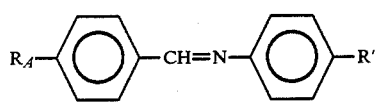

Formula IVk
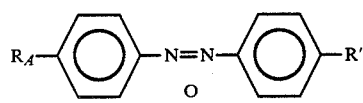

Formula IVl
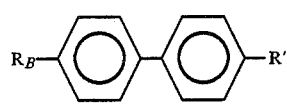

Formula IVm
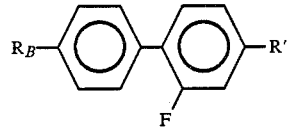

Formula IVn
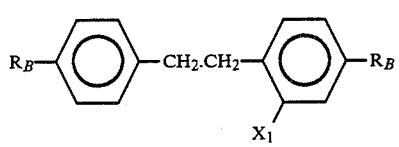

Formula IVo
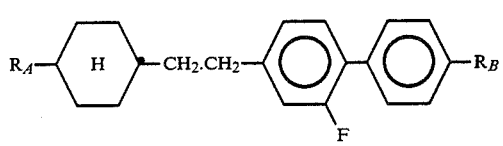

Formula IVp
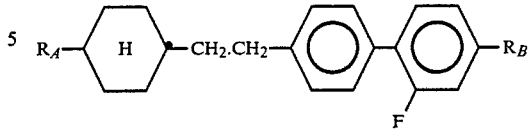

where
 each $R_B$ is independently n-alkyl or n-alkoxy
 each $R_A$ is independently n-alkyl
 each R' is independently n-alkyl, n-alkoxy or hydrogen
 $X_1$ = H or F
and
 Q = halogen, eg Cl or F.

Typically, one or more compounds of Formula II may be added to one or more compounds of Formula IIIa to IIIi optionally together with one or more compounds of Formula IV to IVp.

Additional high clearing point compounds may be included in such mixtures, eg one or more compounds selected from the following classes may be used:

Formula Va
$R_A$—⬡—⬡—⬡—CN

Formula Vb
$R_A$—⬢—CO.O—⬡—⬡—CN

Formula Vc
$R_B$—⬡—⬡—CO.O—⬡—⬡—CN

Formula Vd
$R_B$—⬡—CO.O—⬡—⬡—CN

Formula Ve
$R_A$—⬢—⬡—⬡—CN

Formula Vf
$R_A$—⬢—⬡—⬡—$R_B$

Formula Vg
$R_A$—⬢—⬡—⬡—⬢—$R_A$

Formula Vh
$R_A$—⬢—CO.O—⬡—⬡—$R_B$
              $X_1$

Formula Vi
$R_A$—⬢—CO.O—⬡—⬡—$R_B$
              $X_1$

Formula Vj
$R_A$—⬢—CH$_2$.CH$_2$—⬡—⬡—CN where $R_B$ and $R_A$ and $X_1$ are as defined above.

Other specific known additives, eg chiral additives, such as

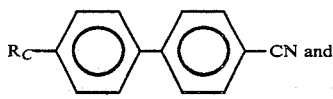

where $R_C=(+)$-2-methylbutyl and $R_D=(+)$-2-methylbutoxy, may be incorporated in the mixture where required.

The liquid crystal material obtained by blending together compounds of Formula II with those of the other classes as specified may be any one of the following:

(i) a positive nematic material for use in twisted nematic effect devices including multiplexed devices; as example of such a device is given below:

(ii) a negative material preferably also with a pleochroic dye, for use in Fréedericksz effect devices (negative nematic type) in which the molecular arrangement may be changed from the homeotropic texture (OFF state) to the homogeneous texture (ON state) by an electric field; an example of such a device is given below:

(iii) a positive nematic material, preferably also with a pleochroic dye, for use in Fréedericksz effect devices (positive nematic type) in which the molecular arrangement may be changed from the homogeneous texture (OFF state) to the homeotropic texture (ON state) by an electric field:

(iv) a negative material which is a cholesteric (chiral nematic) of suitable resistivity (about $10^9$ ohm-cm), for use in cholesteric memory mode devices in which the molecular arrangement may be changed from a homogeneous texture (OFF state) to a scattering focal conic texture (ON state) by an electric field;

(v) a strongly negative material which is a cholesteric, preferably together also with a pleochroic dye, for use in cholesteric-to-nematic phase change effect devices (positive contrast type) in which the molecular arrangement may be changed from a weakly scattering, ie clear, surface aligned homeotropic texture (OFF state) to a strongly scattering twisted homogeneous texture (ON state) by an electric field:

(vi) a positive material which is a cholesteric, preferably together also with a pleochroic dye, in cholesteric-to-nematic phase change effect devices (negative contrast type) in which the molecular arrangement may be changed from a scattering focal conic texture (OFF state) to a clear homeotropic texture (ON state) by an electric field:

(vii) a negative nematic material of suitable resistivity (about $10^9$ ohm-cm), in dynamic scattering effect devices in which the molecular arrangement may be changed from a clear homeotropic texture (OFF state) to a turbulent scattering texture (ON state) by an electric field:

(viii) a positive nematic material in two frequency switching effect devices (which may be twisted nematic effect devices) in which the dielectric anistropy of the material may be changed from (at low frequency) positive (OFF state) to negative (ON state) by the application of a high frequency electric field.

(ix) a material suitable for the device described in copending UK Patent Application No. 8218821.

The construction and operation of the above devices and the general kinds of material which are suitable for use in them are themselves known.

Where a liquid crystal material is for use in a twisted nematic effect, cholesteric to nematic phase change effect (negative contrast type) or Freedericksz effect (positive nematic type) device the material preferably contains:

Component A: one or more compounds of Formula II plus

Component B: one or more compounds of Formula IIIa to IIIf optionally together with one or more of the following:

Component C: one or more compounds of Formula IV to IVp;

Component D: one or more compounds of Formula Va to Vj;

Component E: one or more chiral additives.

For the twisted nematic effect and Freedericksz (positive nematic) effect the following percentages of the various components may be used in the material (the overall sum of the percentages adding to 100%).

Component A: 5 to 95% by weight (typically 5 to 40% by weight)

Component B: 5 to 95% by weight (typically 50 to 80% by weight)

Component C: 0 to 90% by weight (typically 5 to 25% by weight)

Component D: 0 to 30% by weight (typically 0 to 15% by weight)

Component E: 0 to 5% by weight (typically 0 to 1% by weight)

For the phase change (negative contrast type) the following proportions may be used:

Components A to D: in the percentages as specified above;

Component E: 2 to 20% (typically 4 to 5%) by weight.

For the Fréedericksz (positive nemaic) and phase change (negative contrast type) effects a pleochroic dye forming from 1.5 to 15% of the overall mixture is preferably added to the liquid crystal material. Suitable dyes are described in published UK Patent Application Nos. 2081736A, 208219A and 2093475A. Typically, each dye compound incorporated forms 1 to 3% by weight of the overall mixture.

Liquid crystal mixtures including compounds of Formula II may be formed in a known way, eg simply by heating the constituent compounds together in the correct weight proportion to form an overall isotropic liquid (eg at a temperature of about 100° C.).

To provide a more general example of a mixture embodying the invention at least one compound according to Formula II above may be mixed together with one or more compounds in any one or more of the following known families for use in one or more of the applications given above (the actual application(s) depending on the mixture's properties):

i

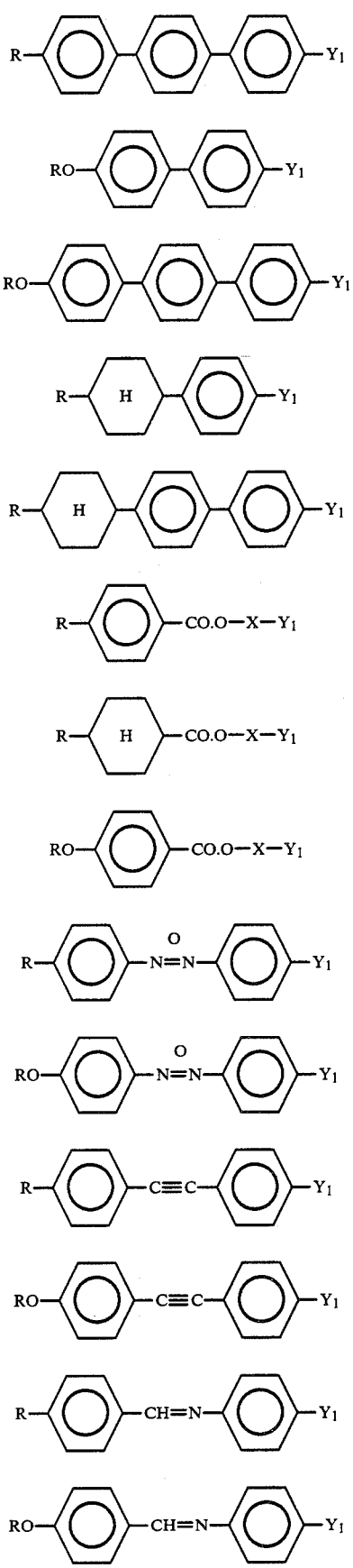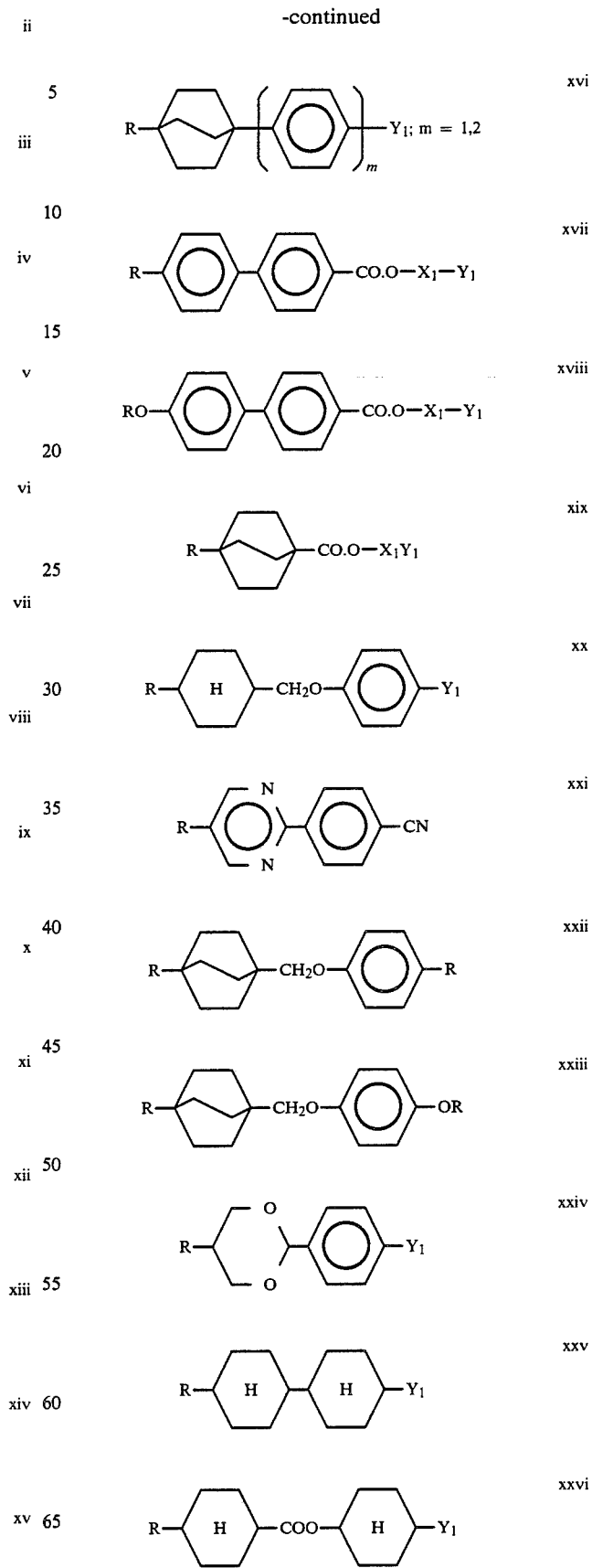

-continued

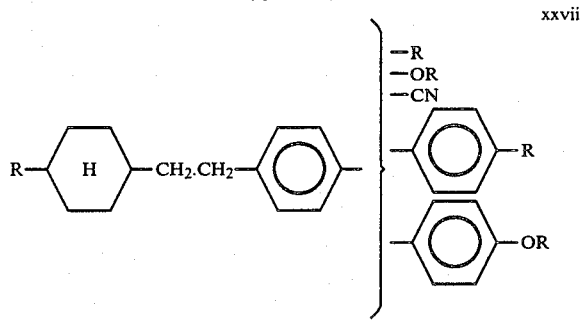

where

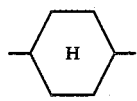

is a trans-1,4-disubstituted cyclohexane ring,

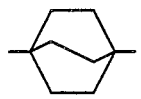

is a 1,4-disubstituted bicyclo(2,2,2)octane ring, X is a 1,4 phenylene group

a 4,4' biphenylyl group

a 2,6 naphthyl group

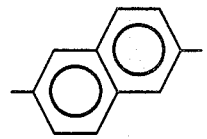

or trans-1,4-disubstituted cyclohexane ring, and $Y_1$ is CN, or R' or halogen CO.O—X—$Y^1$ where $Y^1$ is CN, or R' or OR'; where R and $R^1$ are alkyl groups; or a derivative of one of these wherein H is replaced by a halogen, eg F, in one of the benzene rings.

Preferably, the compound(s) of Formula II comprises between 5 and 95% by weight of the mixture.

According to the present invention in a fourth aspect a liquid crystal device includes two dielectric substrates at least one of which is optically transparent, a layer of liquid crystal material sandwiched between the substrates and electrodes on the inner surfaces of the substrates to enable an electric field to be applied across the layer of liquid crystal material to provide an electro-optic effect therein, characterised in that the liquid crystal material consists of or includes a compound according to Formula II above.

The device according to the fourth aspect may be a twisted nematic effect device, which may or may not be operated in a multiplexed fashion, a cholesteric-to-nematic phase change effect device, a Fréedericksz effect device or a two-frequency switching effect device, all constructed in a known manner or any of the other devices mentioned above. The various ways in which esters of Formula II may be used in these devices are outlined above and will be further apparent to those skilled in the art.

Examples of the preparation and properties of compounds having Formulae I and II will now be given.

EXAMPLE 1

The preparation of 4-[2-(trans-4-n-Pentylcyclohexyl)ethyl]benzoic acid (Formula I, R=n—$C_5H_{11}$)

1-(4-Cyanophenyl)-2-(trans-4-n-pentylcyclohexyl) ethane (10 gram, 35.3 m moles) was added to sulphuric acid (70% w/w 70 ml) and the mixture was stirred and heated at 125°–135° C. for 18 hours. The temperature was then raised to 170° C. and the mixture stirred at this temperature for 3 hours, whereupon no starting material could be detected in the mixture by tlc. Water (120 ml) was added to the cooled mixture which was stirred for 30 minutes. The crude product was filtered off, washed with water (100 ml) and dried in vacuum at 50° C. The yield was 10.6 gram (99% of theory).

The product was recrystallised from acetic acid glacial (50 ml). The crystalline product was washed with water (200 ml) and dried in vacuum at 40° C. the yield was 9.4 gram, (88% of theory), m.p (melting point) 201° C.

EXAMPLE 2

The preparation of 4-[2-(trans-4-Ethylcyclohexyl)ethyl]benzoic acid (Formula I, R=$C_2H_5$)

A procedure similar to that used in Example 1 was followed using 1-(4-cyanophenyl)-2-(trans-4-ethylcyclohexyl)ethane as starting material. The yield of product was 98% of theory and the product's m.p was 215°–200° C.

EXAMPLE 3

The preparation of 4-n-Propylphenyl 4-[2-(trans-4-ethylcyclohexyl)ethyl]benzoate (Formula II; R = $C_2H_5$, X = —⟨○⟩—$C_3H_7$—n)

4-[2-(trans-4-Ethylcyclohexyl)ethyl]-benzoic acid (10.5 gram, 40.38 m moles) prepared as in Example 2 was refluxed with thionyl chloride (60 ml) for 1 hour. The excess thionyl chloride was then distilled off to give 4-[2-(trans-4-ethylcyclohexyl)ethyl]benzoyl chloride (11.2 gram 100% of theory).

The above acid chloride (1.5 gram, 5.39 m moles) was refluxed for 1½ hours with a mixture of 4-n-propylphenol (0.73 gram, 5.39 m moles), triethylamine (3 ml)

and dichloromethane (40 ml). The cooled mixture was then poured into water (40 ml) separated and washed with hydrochloric acid (40 ml, 20%) and water (40 ml). The yield of crude product was 1.8 gram (88.5% of theory).

This was eluted through a column containing silica gel (5 gram) and basic alumina (10 gram) using as solvent a 1:1 mixture of petrol:dichloromethane (200 ml). This gave a yield of 1.6 gram, (79% of theory). Recrystallisation from ethanol (18 ml) gave 4-n-propylphenyl 4-[2-(trans-4-ethylcyclohexyl)ethylcyclohexyl)ethyl]-benzoate, 1.3 gram (64% of theory). This had the following properties: $T_{K-N}$ (melting point or crystal-to-nematic transition temperature)=59.4° C. and $T_{N-I}$ (clearing point)=130.9° C.

EXAMPLE 4

The preparation of 4-n-Propylphenyl 4-[2-(trans-4-n-pentylcyclohexyl)ethyl]-benzoate

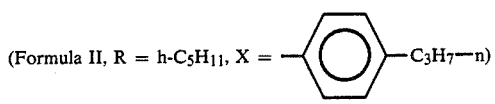

(Formula II, R = h-$C_5H_{11}$, X = —〈O〉—$C_3H_7$—n)

A procedure similar to that used in Example 3 was followed using 4-[2-(trans-4-n-pentylcyclohexyl)ethyl]-benzoic acid prepared as in Example 1 as starting material.

The product had the following properties:
$T_{K-S}$ (crystal to smectic liquid crystal transition temperature)=50° C., $T_{S-N}$ 117° C.
$T_{N-I}$=151.5° C.

EXAMPLE 5

The preparation of 4-n-Butyloxyphenyl 4-[2-trans-4-n-pentylcyclohexyl)ethyl]-benzoate

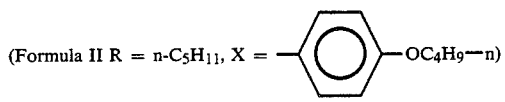

(Formula II R = n-$C_5H_{11}$, X = —〈O〉—$OC_4H_9$—n)

A procedure similar to that used in Example 3 was followed using 4-[2-(trans-4-n-pentylcyclohexyl)ethyl]-benzoic acid and 4-n-butyloxyphenol as starting materials.

The product had the following properties:
$T_{K-S}$=60° C.
$T_{S-N}$ (smectic-to-nematic transition temperature) =144° C.
$T_{N-I}$=167.4° C.

EXAMPLE 6

The preparation of 4-Cyanophenyl 4-[2-(trans-4-n-pentylcyclohexyl)ethyl]-benzoate

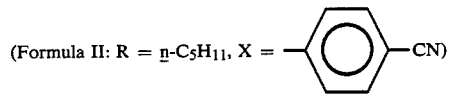

(Formula II: R = n-$C_5H_{11}$, X = —〈O〉—CN)

A procedure similar to that of Example 5 was followed using 4-cyanophenol as starting material.
The product had the following properties:
$T_{K-N}$=79.2° C.

$T_{N-I}$=189.4° C.

EXAMPLE 7

The preparation of 4-fluorophenyl 4-[2-(trans-4-n-ethylcyclohexyl)ethyl]-benzoate

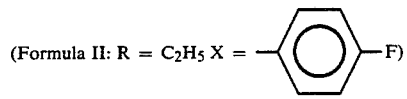

(Formula II: R = $C_2H_5$ X = —〈O〉—F)

A procedure similar to that used in Example 3 was followed using 4-[2-(trans-4-n-ethylcyclohexyl)ethyl]-benzoic acid and 4-fluorophenol as starting materials.

The product had the following properties:
$T_{K-N}$ (melting point or crystal-to-nematic transition temperature)=75.0°→75.2° C. and
$T_{N-I}$ (clearing point)=110.7° C.

The product of Example 3 illustrates the usefulness of the esters of Formula II.

Ten percent by weight of the product of Example 3 (based on the weight of the material to which it was added) was added to the commercial liquid crystal material E7 supplied by BDH Chemicals Ltd. Poole, England and the value of $T_{N-I}$ was raised from 60° C. to 65.5° C. by the addition.

Examples of materials and devices embodying the invention will now be described by way of example only with reference to the accompanying drawings wherein.

Figure 1:
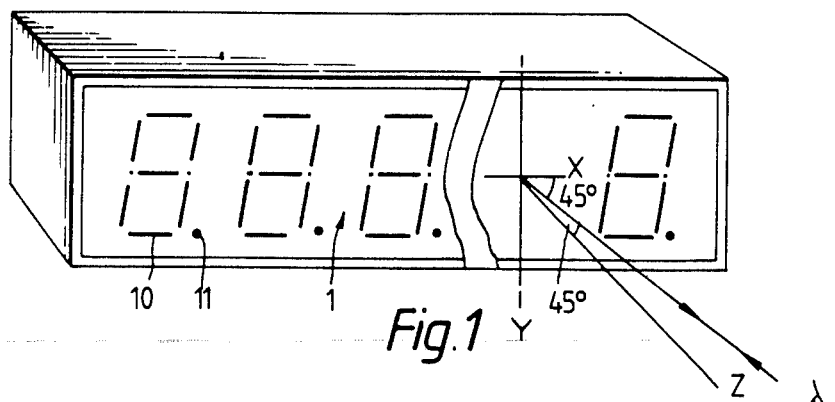
FIG. 1 is a sectional view of a twisted nematic digital display.
Figure 2:
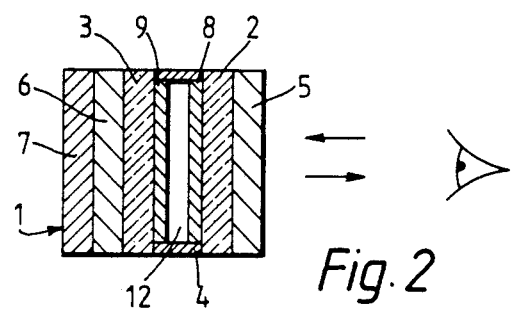
FIG. 2 is a sectional view of the display shown in FIG. 1.

The display of FIGS. 1 to 4 comprises a cell 1, formed of two, front and back, glass slides 2, 3 respectively, spaced about 7 μm apart by a spacer 4 all held together by an epoxy resin glue. A liquid crystal material 12 fills the gap between the slides 2, 3 and the spacer 4. In front of the front glass slide 2 is a front polariser 5 arranged with its axis of polarisation axis horizontal. A reflector 7 is arranged behind the slide 3. A rear polariser 6 or analyser is arranged between the slide 3 and reflector 7.

Figure 3:
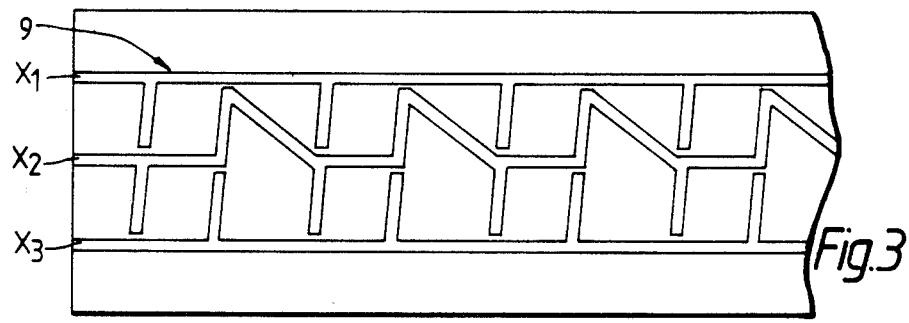
FIG. 3 shows a rear electrode configuration for FIG. 1.
Figure 4:
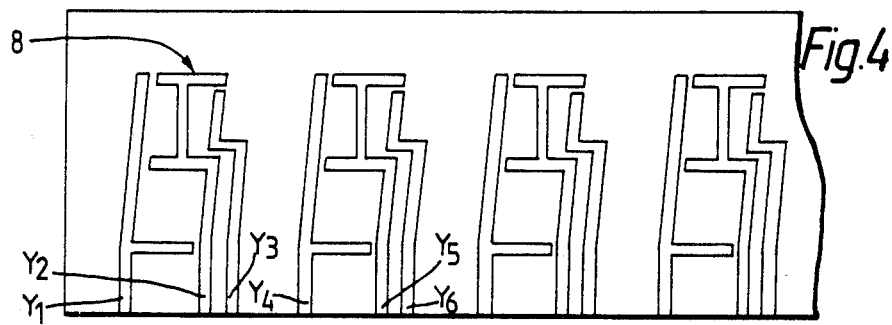
FIG. 4 shows a front electrode configuration for FIG. 1.

Electrodes 8, 9 of tin oxide typically 100 Å thick are deposited on the inner faces of the slides 2, 3 as a complete layer and etched to the shapes shown in FIGS. 3, 4. The display has seven bars per digit 10 plus a decimal point 11 between each digit. As shown in FIG. 3 the rear electrode structure is formed into three electrodes $x_1$, $x_2$, $x_3$. Similarly the front electrode structure is formed into three electrodes per digit and decimal point $y_1$, $y_2$, $y_3$. . . . Examination of the six electrodes per digit shows that each of the eight elements can independently have a voltage applied thereto by application of suitable voltage to appropriate x, y electrodes.

Prior to assembly the slides 2, 3 bearing the electrodes are cleaned then dipped in a solution of 0.2% by weight of poly-vinyl alcohol (PVA) in water. When dry, the slides are rubbed in a single direction with a soft tissue then assembled with the rubbing directions orthogonal to one another and parallel to the optical axis of the respective adjacent polarisers, ie so that the polarisers are crossed. When the nematic liquid crystal material 12 is introduced between the slides 2, 3 the molecules at the slide surfaces lie along the respective rubbing directions with a progressive twist between the slides.

When zero voltage is applied to the cell 1 light passes through the front polarizer 5, through the cell 1 (whilst having its plane of polarisation rotated 90°) through its rear polariser 6 to the reflector 7 where it is reflected back again to an observer (shown in FIG. 1 at an angle of 45° to the axis Z normal to axes X and Y in the plane of the slides 2, 3). When a voltage above a threshold value is applied between two electrodes 8, 9 the liquid crystal layer 12 loses its optical activity, the molecules being re-arranged to lie perpendicular to the slides 2, 3 ie along the axis Z. Thus light at the position does not reach the reflector 7 and does not reflect back to the observer who sees a dark display of one or more bars of a digit 10.

Figure 5:
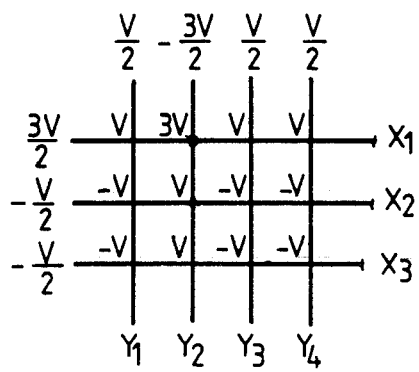
FIGS. 5, 6, 7 show schematic views of the device of FIGS. 1 to 4 with typical addressing voltages.
Figure 6:
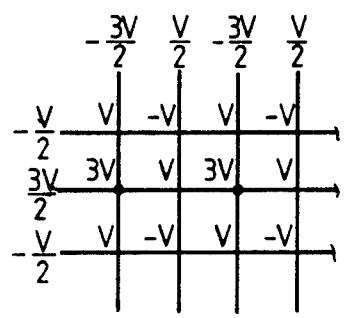
Figure 7:
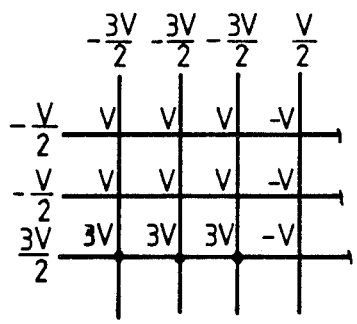

Voltages are applied as follows as shown in FIGS. 5, 6 and 7 for three successive time intervals in a linescan fashion. An electrical potential of 3 V/2 is applied to, ie scanned down, each x electrode in turn whilst −V/2 is applied to the remaining x electrodes. Meanwhile −3 V/2 or V/2 is applied to the remaining x electrodes. Meanwhile −3 V/2 or V/2 is applied to the y electrodes. A coincidence of 3 V/2 and −3 V/2 at an intersection results in a voltage 3 V across the liquid crystal layer 12. Elsewhere the voltage is V or −V. Thus by applying −3 V/2 to appropriate y electrodes as 3 V/2 is scanned down the x electrodes selected intersections are turned ON as indicated by solid circles. The electric voltage V is an ac signal of eg 100 Hz square wave, and the sign indicates the phase.

It will be apparent to those skilled in the art that the device shown in FIGS. 1 to 7 is a multiplexed display because the electrodes are shared between ON and OFF intersections or display elements.

A material embodying the invention which is suitable for use as the material 12 in the above device is in Table 1 as follows (Mixture 1).

TABLE 1

| Mixture 1 | |
|---|---|
| Compound | Weight Percentage |
| C₂H₅─◯─◯─CN | 15 |
| n-C₄H₉─◯─◯─CN | 15 |
| C₂H₅─⟨H⟩─◯─CN | 15 |
| n-C₄H₉─⟨H⟩─◯─CN | 15 |
| n-C₃H₇─⟨H⟩─CH₂.CH₂─◯─◯─C₃H₇─n (F) | 20 |

TABLE 1-continued

| Mixture 1 | |
|---|---|
| Compound | Weight Percentage |
| n-C₂H₅─⟨H⟩─CH₂.CH₂─◯─CO.O─◯─C₃H₇─n | 20 |

Small amounts of an optically active material may be added to the nematic material to induce a preferred twist in the molecules in the liquid crystal layer. This and the use of appropriate slide surface treatment removes the problems of display patchiness as taught in UK Patent Ser. Nos. 1,472,247 and 1,478,592.

Suitable optically active materials are:
C15: about 0.1–0.5% by weight and CB15: about 0.01% to 0.05% by weight.

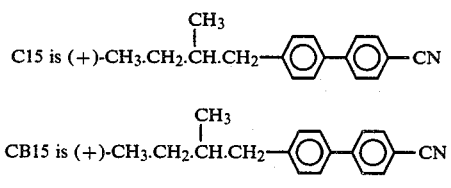

Small amounts of pleochroic dye may be added to enhance the display contrast, eg 2% by weight of dye Mixture 2 specified in UK Patent Specification No. 2093475A. One polariser is removed in this case.

In another embodiment mixtures embodying the second aspect of the invention may be used in a Fréedericksz effect cell. Such a cell may be constructed by sandwiching the liquid crystal material between glass slides having electrode films deposited on their inner surfaces as in the above device. However, in this case the polarisers are not necessary; the glass slide inner surfaces are treated with a coating of lecithin and the liquid crystal material is a negative material whose molecules are aligned in the OFF state perpendicular to the slide substrates (homeotropic texture) by the lecithin coating. Application of an appropriate electric field across the material in the ON state re-arranges the molecules parallel to the slide surfaces (homogeneous texture). A pleochroic dye may be incorporated in the liquid crystal material to enhance the contrast between the ON and OFF states.

A Fréedericksz effect cell made in the above way may incorporate Mixture 2 below, the cell specing being 10 μm.

TABLE 2

| Mixture 2 | |
|---|---|
| Compound | Weight Percentage |
| n-C₅H₁₁─⟨H⟩─CO.O─◯(F)─C₃H₇─n | 30 |
| n-C₄H₉─⟨H⟩─CO.O─◯(F)─C₅H₁₁─n | 30 |
| n-C₂H₅─⟨H⟩─CH₂.CH₂─◯─CO.O─◯─C₃H₇─n | 20 |

TABLE 2-continued

Mixture 2

| Compound | Weight Percentage |
|---|---|
| 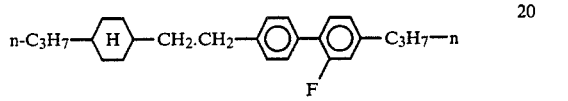 n-C₃H₇—⟨H⟩—CH₂.CH₂—⌬—⌬(F)—C₃H₇—n | 20 |
| Compound A = C₂H₅—⟨H⟩—CO.O—⌬(CN)—O.OC—⟨H⟩—C₂H₅ (with CN on second ring) | | may optionally be added to Mixture 2 (up to 3% by weight of Mixture 2) as a negative additive.

The preparation of Compound A is described in published UK Patent Application No. 2061256A. About 1% by weight of a dye mixture specified above may be added to Mixture 2 to give a dyed mixture. (Mixture 3A)

When a voltage is applied across the cell, the colour changes from a weakly absorbing state to a strongly absorbing state.

In an alternative embodiment of the invention a (cholesteric-to-nematic) phase change effect device incorporates a material as defined above.

A cell is prepared containing a long helical pitch cholesteric material sandwiched between electrode-bearing glass slides as in the twisted nematic cell described above. However the polarisers and surface preparations for homogeneous alignment, eg treatment of the glass slide surfaces with SiO, are not used in this case.

If the glass slides are untreated and the liquid crystal material has a positive dielectric anisotropy ($\Delta\epsilon$) the liquid crystal material is in a twisted focal conic molecular texture in the OFF state which scatters light. The effect of an electric field applied between a pair of electrodes on the respective inner surface of the glass slides is to convert the region of liquid crystal material between the electrodes into the ON state which is a homeotropic nematic texture which is less scattering than the OFF state. This is a 'negative contrast' type of phase change effect device.

If the inner glass slide surfaces are treated, eg with a coating of lecithin, to give alignment perpendicular to those surfaces, and the liquid crystal material has $\Delta\epsilon$ negative the material in the OFF state is in a homeotropic texture which has little scattering effect on incident light. If an electric field is applied between a pair of electrodes on the respective inner surfaces of the glass slides the region of liquid crystal material between the electrodes is converted to a twisted homogeneous texture which scatters light (the ON state). This is a 'positive contrast' type of phase change effect device.

The contrast between the two states in each case may be enhanced by the addition of a small amount of a suitable pleochroic dye (eg 1% by weight of the dye mixture specified above in the case where $\Delta\epsilon$ is positive) to the liquid crystal material.

A suitable positive dielectric anisotropy material, Mixture 3, embodying the invention for use in a phase change effect (negative contrast type) device is:

TABLE 3

Mixture 3

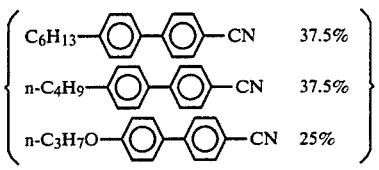

| Compound | | Weight Percentage |
|---|---|---|
| Mixture B { C₆H₁₃—⌬—⌬—CN  37.5%<br>n-C₄H₉—⌬—⌬—CN  37.5%<br>n-C₃H₇O—⌬—⌬—CN  25% } | | 50 |
| n-C₅H₁₁—⟨H⟩—CH₂.CH₂—⌬—⌬(F)—C₂H₅ | | 23 |
| CB15 = R_c—⌬—⌬—CN<br>(R_c = (+)-2-methylbutyl) | | 4 |
| n-C₅H₁₁—⟨H⟩—CH₂.CH₂—⌬—CO.O—⌬—C₃H₇—n | | 23 |

A suitable negative dielectric anisotropy material embodying the invention for use in a phase change effect (positive contrast type) device, Mixture 4, is as follows:

TABLE 4

Mixture 4

| Material | Weight Percentage |
|---|---|
| Mixture 2 | 99 |
| 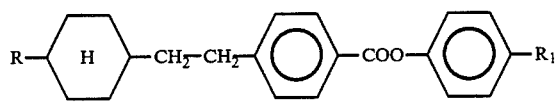 R_c—⌬—⌬—CO.O—⌬—R_c | 1 |

(R_c = (+)-2-methylbutyl)

As an alternative to the chiral compound specified in Table 4 a chiral compound of Formula I may be used.

We claim:

1. A disubstituted ethane having a formula

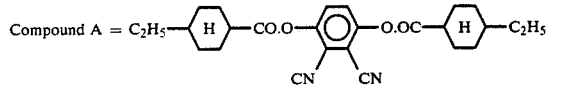

R—⟨H⟩—CH₂—CH₂—⌬—COO—⌬—R₁ wherein R is alkyl and R₁ is selected from the class consisting of hydrogen, alkyl, alkoxy, halo and cyano.

2. A disubstituted ethane as claimed in claim 1, wherein R and R₁ are independently selected from n-alkyl having from 1 to 12 carbon atoms, or n-alkoxy having from 1 to 12 carbon atoms.

3. An ethane as claimed in claim 1, wherein R and R₁ is or includes an alkyl group containing from 1 to 12 carbon atoms and which contains a chiral center.

4. An ethane as claimed in claim 1, wherein R is n-pentyl and R₁ is n-propyl.

5. An ethane as claimed in claim 1, wherein R is ethyl and R₁ is n-propyl.

6. An ethane as claimed in claim 1, wherein R is n-pentyl and R₁ is n-butyloxy.

7. An ethane as claimed in claim 1, wherein R is n-pentyl and R₁ is cyano.

8. An ethane as claimed in claim 1, wherein R is ethyl and $R_1$ is F.

9. A liquid crystal mixture containing at least two compounds, one of which is a compound as claimed in claim 1.

10. A liquid crystal device including two dielectric substrates, at least one of which is optically transparent, a layer of liquid crystal material sandwiched between the substrates, and electrodes on the inner surfaces of the substrates to enable an electric field to be applied across the layer of liquid crystal material to provide an electro-optical effect therein, characterized in that the liquid crystal material is a material as claimed in claim 1.

* * * * *